United States Patent [19]
Vandermeeren et al.

[11] Patent Number: 6,008,024
[45] Date of Patent: *Dec. 28, 1999

[54] MONOCLONAL ANTIBODIES SPECIFIC FOR PHF-TAU, HYBRIDOMAS SECRETING THEM, ANTIGEN RECOGNITION BY THESE ANTIBODIES AND THEIR APPLICATIONS

[75] Inventors: Marc Vandermeeren, Geel; Eugeen Vanmechelen, Nazareth; André Van De Voorde, Lokeren, all of Belgium

[73] Assignee: Innogenetics, N.V., Ghent, Belgium

[ * ] Notice: This patent is subject to a terminal disclaimer.

[21] Appl. No.: 08/666,360

[22] PCT Filed: Dec. 14, 1994

[86] PCT No.: PCT/EP94/04146

§ 371 Date: Jun. 20, 1996

§ 102(e) Date: Jun. 20, 1996

[87] PCT Pub. No.: WO95/17429

PCT Pub. Date: Jun. 29, 1995

[30] Foreign Application Priority Data

Dec. 21, 1993  [EP]  European Pat. Off. .............. 93403133

[51] Int. Cl.⁶ ............................ C12P 21/04; C12P 21/08; C12N 5/00; C07K 16/00
[52] U.S. Cl. ...................... 435/70.21; 435/331; 436/548; 530/387.9; 530/388.1
[58] Field of Search ................................ 435/70.21, 331; 436/547, 548; 530/387.9, 388.1, 389.1, 808

[56] References Cited

FOREIGN PATENT DOCUMENTS

| | | |
|---|---|---|
| 1302250 | 6/1992 | Canada . |
| 0544942 | 6/1993 | European Pat. Off. . |
| WO9308302 | 4/1993 | WIPO . |

OTHER PUBLICATIONS

Goedert et al., "The abnormal phosphorylation of tau protein at Ser–202 in Alzheimer disease recapitulates phosphorylation during development", *Proceedings of the National Academy of Sciences of the USA*, vol. 90, No. 11, Jun. 1, 1993, Washington, D.C., pp. 5066–5070.

Ghanbari et al., "Detection and Measurement of Alzheimer's Disease–Associated Protein (ADAP) in Cerebrospinal Fluid (CSF): An Antemortem Marker for Alzheimer Disease", *Society for Neuroscience, Symposia*, vol. 17, 1991, Bethesda, MD, p. 1259.

Goedert et al., "Cloning and sequencing of the cDNA encoding an isoform of microtubule–associated protein tau containing four tandem repeats: differential expression of tau protein mRNAs in human brain", *The Embo Journal*, vol. 8, No. 2, Feb. 1989, Oxford, GB, pp. 393–399.

Vandermeeren et al., "Detection of t Proteins in Normal and Alzheimer's Disease Cerebrospinal Fluid with a Sensitive Sandwich Enzyme–Linked Immunosorbent Assay", *Journal of Neurochemistry*, vol. 61, No. 5, Nov. 1993, New York, NY pp. 1828–1834.

Vandermeeren et al, (Journal of Neurology, 61: 1828–1834, 1993.

Mercken et al, Acta Neuropathol, 84: 265–272, 1992.

Hasegawa et al, Journal of Neurochemistry, 60: 2068–2077, 1993.

Harlow et al "Antibodies, A Laboratory Manual", Cold Spring Harbor Laboratory Press, 1988 pp. 271–276.

*Primary Examiner*—Patricia A. Duffy
*Attorney, Agent, or Firm*—Greer, Burns & Crain

[57] ABSTRACT

Monoclonal antibody AT180 secreted by the hybridoma deposited at ECACC on Dec. 22, 1992 under No. 92122204, and monoclonal antibody AT270 secreted by the hybridoma deposited at ECACC on Jul. 7, 1993 under 93070774, each of which forms an immunological complex with a phosphorylated epitope of an antigen belonging to abnormally phosphorylated tau protein (PHF-tau) residing in the region spanning positions 143-254 with the following amino acid sequence:

```
          143                        150
NH₂ - Lys Gly Ala Asp Gly Lys Thr Lys Ile
                                 160
    Ala Thr Pro Arg Gly Ala Ala Pro Pro Gly
                                 170
    Gln Lys Gly Gln Ala Asn Ala Thr Arg Ile
                                 180
    Pro Ala Lys Thr Pro Pro Ala Pro Lys Thr
                                 190
    Pro Pro Ser Ser Gly Glu Pro Pro Lys Ser
                                 200
    Gly Asp Arg Ser Gly Tyr Ser Ser Pro Gly
                                 210
    Ser Pro Gly Thr Pro Gly Ser Arg Ser Arg
                                 220
    Thr Pro Ser Leu Pro Thr Pro Pro Thr Arg
                                 230
    Glu Pro Lys Lys Val Ala Val Val Arg Thr
                                 240
    Pro Pro Lys Ser Pro Ser Ser Ala Lys Ser
                                 250
    Arg Leu Gln Thr Ala Pro Val Pro Met Pro

Asp Leu Lys COOH
``` with each monoclonal antibody specifically detecting abnormally phosphorylated tau protein (PHF-tau) in cerebrospinal fluid (CSF).

8 Claims, 3 Drawing Sheets

MONOCLONAL ANTIBODIES SPECIFIC FOR PHF-TAU, HYBRIDOMAS SECRETING THEM, ANTIGEN RECOGNITION BY THESE ANTIBODIES AND THEIR APPLICATIONS

The invention relates to new monoclonal antibodies specific for PHF-tau, to the hybridomas secreting these monoclonal antibodies, and to the antigen recognition pattern of these monoclonal antibodies and their applications. The invention also relates to a process for diagnosing brain diseases involving monoclonal antibodies of the invention, more particularly in cerebrospinal fluid (CSF) samples. The invention also relates to a region of the tau molecule modifiable in vivo by the process of phosphorylation, which is found to be associated with Alzheimer's disease or with other types of dementia and which is specifically recognized by the monoclonal antibodies of the invention.

Alzheimer's disease (AD) is the most common form of adult-onset dementia. At present, no reliable biochemical test is available for antemortem diagnosis of AD. The disease is therefore diagnosed clinically on the basis of exclusion of other forms of dementia. The diagnosis can be confirmed neuropathologically by the demonstration of large amounts of neuritic (senile) plaques and neurofibrillary tangles (NFT) in particular brain regions (McKhann et al, 1984).

Neurofibrillary tangles consist of paired helical filaments (PHFs). Immunocytochemical evidence suggests that the microtubule-associated protein tau is a major protein component of PHF and NFT (Brion et al., 1985b; Delacourte and Defossez, 1986; Grundke-Iqbal et al., 1986; Kosik et al., 1986; Wood et al., 1986). Definite proof that the tubulin-binding domain of tau is tightly associated with the core of PHFs was obtained via amino acid sequencing (Kondo et al., 1988). Nevertheless it has been suggested that tau peptides may represent only a small portion of the major component of PHF (Wischik et al., 1988).

Tau protein exists in different isoforms, of which 4 to 6 are found in adult brain but only 1 isoform is detected in fetal brain. The diversity of the isoforms is generated from a single gene on human chromosome 17 by alternative mRNA splicing (Andreadis et al., 1992). The most striking feature of tau protein, as deduced from molecular cloning, is a stretch of 31 or 32 amino acids, occurring in the carboxy-terminal part of the molecule, which can be repeated either 3 or 4 times. Additional diversity is generated through 29 or 58 amino acid-long insertions in the $NH_2$-terminal part of tau molecules (Goedert et al., 1989). For simplicity, all numbering in this patent application refers to the tau variant htau40 containing all exons (441 amino acids long) according to Goedert et al (1989).

Under normal circumstances tau promotes microtubule assembly and stability in the axonal compartment of neurons. The microtubule-binding domain in tau is localized in the repeat region of tau (255–381) (Lewis et al, 1990) and is modulated by adjacent regions: the carboxyterminal tail (382–414) and the proline-rich region (143–254) (Drubin & Kirschner, 1991). Stability and bundling of the microtubules is mediated by a short hydrophobic zipper in the carboxy-terminal tail of tau (Lewis et al, 1989). Both assembly and stability are regulated by alternative mRNA splicing and phosphorylation.

In normal circumstances adult brain contains 2 to 3 mol phosphate per mole of tau (Selden and Pollard, 1983; Ksiezak-Reding et al, 1992) present amongst others at serine 404 (Poulter et al, 1993), while other results demonstrate that phosphorylation of different sites in normal tau follows different developmental profiles (Lee et al, 1991; Bramblett et al, 1993; Goedert et al, 1993a). Abnormal tau variants of 60, 64 and 68 kDa have been detected exclusively in brain areas showing neurofibrillary changes and senile plaques (Delacourte et al, 1990). The abnormal electrophoretical behavior of tau is due to phosphorylation since alkaline phosphatase treatment of these tau molecules changes their molecular mass to that of normal tau (Goedert et al., 1992; Flament et al., 1990b, Greenberg & Davies, 1990). Currently abnormal phosphorylation sites have been detected in PHF-tau at positions 46, 231, 235, 263 and 396 (Iqbal et al., 1989; Lee et al., 1991; Hasegawa et al., 1992). In four of these sites, the phosphorylated residu is followed by a proline residu, indicating that a proline-directed kinase is involved in some of the abnormal phosphorylations of tau. In addition to these sites ten others are present in htau40, two of which are also abnormally phosphorylated, as indicated by antibody reactivity (Mab tau2: Watanabe et al., 1992; Mab AT8: Biernat et al., 1992, Goedert et al., 1993).

The abnormal phosphorylation of tau in Alzheimer's disease is due to a shift in the phosphatase/kinase equilibrium. In vitro several kinases can phosphorylate tau: cdc2-kinases (Vulliet et al, 1992; Ledesma et al, 1992), MAP kinases (Drewes et al, 1992, Roder and Ingram, 1991), glycogen synthase kinases (Mandelkow et al, 1992) and TPKI and TPKII (Ishiguro et al, 1992). The phosphatases are less well studied in Alzheimer's disease and so far only one phosphatase was able in vitro to dephosphorylate the abnormally phosphorylated sites, namely protein phosphatase $2A_1$ (Goedert et al, 1992).

So far, the detection of PHF-tau in brain extracts, either via antibodies (Mab Alz50: Ghanbari et al., 1990; Mab Ab423: Harrington et al., 1991), or via the change in molecular weight (Flament et al., 1990, Delacourte et al., 1993), or else by functional assay (Bramblett et al., 1992) has been very useful to discriminate dementia with altered cytoskeletal properties from normal aged subjects or from patients with other types of dementia. Nevertheless the detection of PHF-tau in CSF remained impossible, even using antibodies directed at one of the abnormally phosphorylated sites such as serine 202 (Goedert et al., 1993). This can be ascribed to one or more of the following reasons: 1) the low concentration of PHF-tau in CSF, 2) non-even use of phosphorylation sites among all the potential phosphorylation sites, 3) differences in phosphatase sensitivity of these sites, and, 4) too low an affinity constant of the antibodies used.

The aim of the present invention is therefore to provide monoclonal antibodies which allow the reliable and sensitive detection of abnormally phosphorylated tau present in cerebrospinal fluid.

The invention also aims at providing the hybridomas which secrete the above-said monoclonal antibodies.

The invention furthermore aims at providing the epitopes of the abnormally phosphorylated tau protein present in brain homogenates or in body fluids such as cerebrospinal fluid, which are recognized by said monoclonal antibodies.

Finally, the invention aims at providing a process for the detection or diagnosis in vitro of brain diseases involving abnormally phosphorylated tau proteins.

The present invention relates more particularly to a monoclonal antibody which forms an immunological complex with a phosphorylated epitope of an antigen belonging to abnormally phosphorylated tau (PHF-tau) residing in the region spanning positions 143–254 with the following amino acid sequence:

```
                                             (SEQ ID NO 1)
        143                              150
  NH2- Lys Gly Ala Asp Gly Lys Thr Lys Ile Ala

160
  Thr Pro Arg Gly Ala Ala Pro Pro Gly Gln Lys Gly

170
  Gln Ala Asn Ala Thr Arg Ile Pro Ala Lys Thr Pro

180
  Pro Ala Pro Lys Thr Pro Pro Ser Ser Gly Glu Pro 190                              200
  Pro Lys Ser Gly Asp Arg Ser Gly Tyr Ser Ser Pro

210
  Gly Ser Pro Gly Thr Pro Gly Ser Arg Ser Arg Thr

220
  Pro Ser Leu Pro Thr Pro Pro Thr Arg Glu Pro Lys

230
  Lys Val Ala Val Val Arg Thr Pro Pro Lys Ser Pro

240
  Ser Ser Ala Lys Ser Arg Leu Gln Thr Ala Pro Val

250
  Pro Met Pro Asp Leu Lys COOH
``` and with said monoclonal antibody being characterized by the the fact that it is capable of specifically detecting abnormally phosphorylated tau protein (PHF-tau) in cerebrospinal fluid (CSF).

The monoclonal antibodies of the invention were selected from a range of monoclonal antibodies obtained by direct immunization with PHF-tau, extracted from human brain tissue derived from Alzheimer patients. More particularly the monoclonal antibodies of the invention are characterized by the fact that they specifically bind to naturally occuring abnormally phosphorylated tau. Further analysis of their epitopes showed that the monoclonal antibodies of the invention are directed at phosphorylated epitopes confined to a particular region of the tau molecule, namely the region between 143 and 254 including several potential phosphorylation sites such as T153 and S235 used by the SP and TP directed kinases. The monoclonal antibodies of the invention are further characterized by the fact that they recognize epitopes which are different from the epitope of the monoclonal antibody AT8 as defined in Goedert et al. (1993) and upon comparison with the AT8 antibodies allow the detection of PHF-tau in CSF. They recognize preferentially PHF-tau either on brain sections. immunoblots or in ELISA and they are surprisingly able to detect PHF-tau in CSF, either alone or in combination with other PHF-tau specific antibodies.

In conclusion, the monoclonal antibodies of the invention are characterized in that they specifically bind to naturally occuring abnormally phosphorylated tau of which the phosphorylation state is confined to a particular region of the tau molecules as specified above, or bind to recombinant non-phosphorylated tau after treatment with proline-directed kinases, which can provoke the phosphorylation of, amongst others, Ser-Pro or Thr-Pro sites in the region as specified. Proline-directed kinases such as MAP kinases (Sturgill et al., 1991), cdc2 kinases (Labbe et al., 1991) and glycogen synthase kinases (Vandenheede et al., 1980) can be purified from various tissues or can be present in brain extracts. The phosphorylation of tau by these kinases is abolished or greatly diminished when one or more of the following serines/threonines are mutated to an amino acid such as Ala: T153, T175, T181. S199, S202, T205, T212, T217, T231, or S235. Consequently, the epitope of these antibodies can be characterized via such mutant tau, or via non-phosphorylated tau such as procaryotically expressed recombinant tau and their phosphorylated homologues, or via synthetic peptides having the same amino acid sequence as parts of the region specified above of the human tau 40 protein and with said peptides being capable of being phosphorylated by said kinases or being incapable of being phosphorylated upon synthesis of the peptides. The epitopes of the present invention are thus defined as the proline rich-region of tau between position 143 and 254 and which can be abnormally phosphorylated at threonine 153 (T153), T175, T181, S199, S202, T205, T212, T217, T231 and S235 or a combination of these sites included in the epitope of these antibodies, further referred to as a "PHF-tau epitopes".

The expression "specifically detecting abnormally phosphorylated tau protein" corresponds to the fact that the monoclonal antibodies of the invention detect abnormally phosphorylated tau in CSF without cross-reacting with normal tau present in CSF.

The expression "form an immunologically complex with" means that the monoclonal antibody of the invention binds to the above-said antigen under conditions as mentioned in one of the following techniques:

Light Immunomicroscopy

Brain tissue samples, of e.g. Alzheimer patients obtained at surgery or autopsy, are fixed by immersion in 4% formalin or Bouin's fixative and embedded in paraffin for sectioning. The monoclonal antibodies of the invention are applied in conjunction with a technique to visualize the formed immune complexes such as the avidin-biotinylated peroxidase complex technique (Hsu et al., 1981) using 3,3'-diaminobenzidine tetrahydrochloride for development of color. Sections are counterstained with Harris haematoxylin stain.

Immunoelectron Microscopy in Tissue Sections

Brain tissue samples e.g. obtained from Alzheimer patients at surgery or autopsy are fixed in either Bouin's fixative or 10% buffered formalin before sectioning without embedding (Vibratome). The monoclonal antibody of the invention is used for immunostaining by the indirect immunogold method after which the sections are fixed, embedded and sectioned for electron microscopy, all according to standard protocols known to those skilled in the art (Brion et al., 1985a).

Immunoblotting Procedures

For immunoblotting, fractions enriched in PHF-tau are prepared as described (Greenberg and Davies, 1990). Typically, postmortem tissue, consisting mostly of gray matter from the frontal and temporal cortex, was obtained from histologically confirmed Alzheimer patients. This Alzheimer gray matter brain sample (5–10 g) was homogenized with 10 volumes of cold buffer H (10 mM Tris/1 mM EGTA/0.8 M NaCl/10% sucrose, pH 7.4) in a Teflon/glass Potter S (Braun, Germany) homogenizer. After centrifugation of the homogenate in a 60 Ti MSE rotor at 27,000×g for 20 min at 4° C., the pellet was removed and the supernatant was adjusted to 1% (wt/vol) N-laurosylsarcosine and 1% (vol/vol) 2-mercaptoethanol and incubated while rotating on a mixer (Swelab, Sweden) for 2.5 hours at 37° C. The supernatant mixture was centrifuged at 108,000×g for 35 min at 20° C. The PHF-tau containing pellet was gently washed with PBS and finally suspended in 1 ml of the same buffer.

SDS-polyacrylamide electrophoresis is performed under reducing conditions on 12% gels (Laemmli, 1970). After electrophoresis, the proteins are either fixed and stained with Coomassie brilliant blue, or transferred (Towbin et al., 1979) to nitrocellulose sheets (Hybond-C. Amersham) or Immobilon filters (Millipore).

After transfer, the filters are presoaked in PBS containing 0.05% (v/v) Tween 20 (Tween-PBS) and then incubated for 1 h in Tween-PBS containing 5% (w/v) skimmed dried milk and 10% (v/v) newborn calf serum (blocking buffer). Next, the filters are treated overnight at 4° C. with a monoclonal antibody according to the invention appropriately diluted in blocking buffer.

The filters are then washed three times in Tween-PBS and treated for 1.5 h at room temperature with horseradish peroxidase-labeled rabbit anti-mouse IgG (Dakopatts, Denmark) diluted 1/3000 in blocking buffer. After three washes in Tween-PBS, streptavidine-biotinylated horseradish peroxidase complex (Amersham), diluted 1/250 in blocking buffer, is applied for 1.5 h at room temperature. Thereafter, the filters are washed three times in Tween-PBS and once in PBS. The filters are then incubated in PBS containing 0.05% (w/v) diaminobenzidine and 0.03% (v/v) hydrogen peroxide until background staining develops.

It should be clear that the formation of an immunological complex between the monoclonal antibodies and the antigen is not limited to the precise conditions described above, but that all techniques that respect the immunochemical properties of the antibody and antigen binding will produce similar formation of an immunological complex.

The present invention relates more particularly to a monoclonal antibody as defined above, characterized by the fact it forms an immunological complex:
  either with a phosphorylated epitope located within the sequence defined above (SEQ ID NO 1),
  or with any other phosphorylated peptide capable of forming an immunological complex with a monoclonal antibody, which itself is capable of forming a complex with a phosphorylated epitope located in the human tau protein region as shown in SEQ ID NO 1.

Preferred monoclonal antibodies of the invention, AT180 and AT270, are produced by hybridomas deposited at ECACC (European Collection of Animal Cell Cultures, Vaccine Research and Production Laboratory, Public Health and Laboratory Service (PHLS), Centre for Applied Microbiology and Research, Porton Down, GB-Salisbury, Wiltshire SP4 OJG) United Kingdom, on Dec. 22, 1992, under No. 92122204 or on Jul. 7, 1993 under No. 93070774.

The above-mentioned monoclonal antibodies are obtained by a process involving obtention and isolation of hybridomas which secrete these monoclonal antibodies.

The preferred monoclonal antibodies of the invention allow the detection of at least 1, 5, 10 or 20 pg/ml phosphorylated tau as determined in an ELISA using these monoclonal antibodies in the coating phase and incubating them with CSF spiked with different amounts of phosphorylated and non-phosphorylated tau without amplification. Phosphorylated tau is prepared by incubating recombinant non-phosphorylated tau with a rat brain extract capable of phosphorylation of Ser and Thr amino acids at positions corresponding to sites of abnormal phosphorylation of tau (Goedert et al., 1993), as found in tau extracts of brain tissue derived of patients having died of Alzheimer's disease.

A process for obtaining the hybridomas of the invention involves:
  starting from spleen cells of an animal, e.g. mouse or rat, previously immunized in vivo or from spleen cells of such animals previously immunized in vitro with an antigen being preferably abnormally phosphorylated tau (PHF-tau), or a phosphorylated human tau peptide or immunoaffinity purified abnormally phosphorylated tau, as disclosed below, recognized by the monoclonal antibodies of the invention;
  fusing said immunized cells with myeloma cells under hybridoma-forming conditions; and
  selecting those hybridomas which secrete the monoclonal antibodies which are capable of specifically recognizing a phosphorylated epitope of abnormally phosphorylated tau (PHF-tau) in cerebrospinal fluid (CSF).

The phosphorylated human tau peptide refers to a peptide comprising in its amino acid sequence a phosphorylated sequence comprised in the region spanning amino acids 143 to 254 of human tau and with said peptide being characterized by the fact that it can form an immunological complex with the antibodies of the invention.

The antigen of the invention is advantageously contained in the brain, in the cerebrospinal fluid or the serum of a patient having Alzheimer's disease, Down syndrome, Pick's disease, subacute sclerosing panencephalitis (SSPE) or other neurological diseases in which the abnormally phosphorylated tau protein is implicated; this antigen provokes an immunological reaction with the monoclonal antibody of the invention.

More particularly, the present invention relates also to monoclonal antibodies as defined above, obtained by a process such as defined above, characterized in that it involves:
  starting from the spleen cells of a mouse previously immunized with abnormally phosphorylated tau (PHF-tau) extracted and purified from a human brain sample of a patient suffering from Alzheimer's disease (as disclosed in the examples section), or a phosphorylated human tau peptide, or immunoaffinity-purified abnormally phosphorylated tau capable of reacting with the monoclonal antibodies of the invention,
  fusing said immunized cells with myeloma cells under hybridoma-forming conditions,
  selecting those hybridomas which secrete monoclonal antibodies which specifically recognize PHF-tau and which are capable of specifically detecting PHF-tau in CSF (as illustrated in detail in the examples section).

A process for producing the monoclonal antibodies of the invention involves:
  culturing the selected hybridomas as indicated above in an appropriate culture medium; and
  recovering the monoclonal antibodies secreted by said selected hybridoma; or alternatively
  implanting the selected hybridoma into the peritoneum of a mouse and, when ascites has been produced in the animal;
  recovering the monoclonal antibodies then formed from said ascites.

The monoclonal antibodies of the invention can be prepared by conventional in vitro techniques such as the culturing of immobilized cells using e.g. hollow fibers or microcapsules or such as the culturing of cells in homogeneous suspension using e.g. airlift reactors or stirred bioreactors.

The invention also relates to a peptide capable of forming an immunological complex with any of the monoclonal antibodies of the invention, with said peptide being in the phosphorylated form, and,
  with the sequence of said peptide comprising, or consisting of phosphorylated parts of the sequence as shown in SEQ ID NO 1, or, with the sequence of said peptide comprising, or consisting of the sequence of any peptide being capable of forming an immunological complex with anyone of the monoclonal antibodies according to the invention.

Said phosphorylated peptides are preferably from 6 to 100 amino acids long. The peptides according to this embodiment of the invention can be prepared by classical chemical synthesis. The synthesis may be carried out in homogenous solution or in solid phase according to any of the techniques well known in the art.

Phosphorylated peptides are prepared according to any technique known in the art, (f. i. de Bont et al., 1990a; de Bont et al., 1990b; Perich, 1991; Otvos et al., 1989).

According to a preferred embodiment, the present invention relates to a phospohorylated peptide as defined above consisting of or comprising in its amino acid sequence the following sequence:

Val-Arg-Thr-Pro-Pro (amino acid 229–233; human tau 40 numbering, SEQ ID NO 2), with said Thr(231) being phosphorylated and with said peptide being characterized in that it is able to form an immunological complex with the monoclonal antibody AT180 produced by the hybridoma deposited at the ECACC on Dec. 22, 1992 under No. 92122204.

According to another preferred embodiment, the present invention relates also to a phosphorylated peptide as defined above consisting of or comprising in its amino acid sequence the following sequence:

Pro-Lys-Thr-Pro-Pro (amino acid 179–183; human tau 40 numbering; SEQ ID NO 3), with said Thr(181) being phosphorylated and with said peptide being characterized in that it is able to form an immunological complex with the monoclonal antibody AT270 produced by the hybridoma deposited at the ECACC on Jul. 7, 1993 under No. 93070774.

According to yet another embodiment, the present invention relates to a phosphorylated peptide as defined above, which is capable of generating a monoclonal antibody according to any one of claims 1 to 4 upon immunization.

The peptides used for immunization are preferentially in the form in which they are joined to a carrier molecule in order to achieve a good immunogenic response. Such carrier molecules are well known in the art and are coupled to the peptide via linker groups, which are also comprised in the art.

The invention also relates to a process for the post-mortem detection or diagnosis in vitro of a brain/neurological disease involving PHF-tau, such as Alzheimer's disease, which comprises at least the following steps:

contacting a monoclonal antibody of the invention with a preparation of NFT or a detergent-extracted brain homogenate isolated from a patient having had Alzheimer's disease or any other disease involving abnormally phosphorylated tau protein (PHF-tau) under conditions suitable for producing an antigen-antibody complex;

detecting the immunological binding of said antibody to said brain homogenate, and possibly separating said complex and recovering the antigen sought in a purified form.

Recovering the antigen sought may be done by first washing the immobilized antibody-antigen complex then formed;

treating this complex with a solution (e.g. 3 M potassium thiocyanate, 2.5 M magnesium chloride, 0.2 M citrate-citric acid, pH 3.5 or 0.1 M acetic acid) capable of producing the dissociation of the antigen-antibody complex; and;

recovering the antigen in a purified form.

The invention relates also to a process for the detection or diagnosis in vitro of brain/neurological disease involving abnormally phosphorylated tau protein, such as in Alzheimer's disease, which includes:

bringing a sample of CSF, more preferably unconcentrated CSF, or a sample of serum from a patient suspected of suffering from brain disease involving PHF-tau, more particularly Alzheimer's disease, or proteins or polypeptides as a result of an extraction procedure starting from brain tissues, cerebrospinal fluid or serum known to those skilled in the art (Ibqal et al., 1984; Greenberg & Davies, 1990) into contact under in vitro conditions with a monoclonal antibody of the invention, with said conditions being suitable for producing an antigen-antibody complex; and, detecting the immunological binding of said antibody to said sample of brain extract, cerebrospinal fluid or serum, or proteins or polypeptides.

Advantageously, the monoclonal antibodies of the invention are in an immobilized state on a suitable support such as a resin. Alternatively, the present process may be put into practice by using any other immunoassay format known to the person skilled in the art.

The process for the detection of the antigen can then be carried out for instance as follows:

bringing together said antigen-antibody complex formed by the antigen and the antibodies of the invention with:

a second antibody which can be a monoclonal antibody recognizing an epitope of abnormally phosphorylated tau protein, or an epitope of any phosphorylated tau peptide carrying an epitope, with said epitopes being different from the one of the invention, or which can be a polyclonal antibody recognizing abnormally phosphorylated tau or a polyclonal antibody recognizing a peptide carrying an epitope of PHF-tau, with said polyclonal antibody being capable of forming an immunological complex with epitopes which are different from the epitope of the invention with said polyclonal antibody being preferably purified by immunoaffinity chromatography using immobilized tau protein;

a marker either for specific tagging or coupling with said second antibody, with said marker being any possible marker known to the person skilled in the art;

appropriate buffer solutions for carrying out the immunological reaction between the monoclonal antibody of the invention and a test sample on the one hand, and the bound second antibody and the marker on the other hand.

The detection of the immunologically bound monoclonal antibody can be achieved by conventional technology comprised in the art. Advantageously, the second antibody itself carries a marker or a group for direct or indirect coupling with a marker.

The monoclonal antibodies of the invention also enable the diagnosis of Alzheimer's disease (AD) and of any disease involving the formation of abnormally phosphorylated tau in the region 143 to 254 on the basis of CSF (i.e. to detect modified forms of tau in CSF). The problem associated herewith is that this antigen is present in a very low amount in CSF, so the detection assay must be very sensitive. This sensitivity problem may be further overcome by (i) using a combination of the monoclonal antibodies of the invention, or (ii) a combination of a monoclonal antibody of the invention with any other normal and/or abnormally phosphorylated tau monoclonal antibodies known in the art and/or (iii) by using a monoclonal antibody or a combination of monoclonal antibodies of the invention in combination with an amplification technique such as the catalyzed reporter deposition amplification technique (CARD, Bobrow et al., 1989), allowing a PHF-tau specific ELISA with a higher sensitivity.

The results obtained with the monoclonal antibodies of the invention indicate that elevated PHF-tau levels are found in AD, but may occur also in other neurological diseases where abnormal phosphorylation of tau occurs in the region of tau comprised by amino acids 143 to 254.

According to another embodiment, the present invention relates to a kit for the diagnosis in vitro of one of the following diseases: Alzheimer's disease, Down's syndrome, Pick's disease and other neurological disorders in which abnormally phosphorylated tau protein or paired helical filaments are implicated, characterized in that the kit comprises:

- at least one monoclonal antibody of the invention deposited on a microplate;
- a preparation containing the sample (CSF, serum or the proteins extracted therefrom) to be diagnosed in vitro,
- a second antibody
    which can be a monoclonal antibody recognizing an epitope of abnormally phosphorylated tau protein, or an epitope of any phosphorylated tau peptide carrying an epitope, with said epitopes being different from the one of the invention, or
    which can be a polyclonal antibody recognizing abnormally phosphorylated tau or a polyclonal antibody recognizing a peptide carrying an epitope of PHF-tau, with said polyclonal antibody being capable of forming an immunological complex with epitopes which are different from the epitope of the invention, with said polyclonal antibody being preferably purified by immunoaffinity chromatography using immobilized tau protein;
- a marker either for specific tagging or coupling with said second antibody;
- appropriate buffer solutions for carrying out the immunological reaction between the monoclonal antibody of the invention and a test sample on the one hand, and the bound second antibody and the marker on the other hand,
- possibly a peptide carrying an epitope of PHF-tau comprised in the region spanning amino acids 143 to 254 for standard purposes, or for competition purposes with respect to the antigen which is sought.

A preferred embodiment of the present invention for the detection or diagnosis in vitro of brain/neurological disease involving abnormally phosphorylated tau protein, such as Alzheimer's disease relates to a method or a kit as defined above, which comprises a mixture (combination) of monoclonal antibodies of the invention, or a combination of at least one monoclonal antibody of the invention with other antibodies capable of specifically recognizing a region of PHF-tau residing in the region spanning positions 143–254 of human tau 40 (SEQ ID NO 1), with said monoclonal antibodies being preferably chosen from:

(1) the monoclonal antibody AT180 produced by the hybridoma deposited at the ECACC on Dec. 22, 1992 under No. 92122204;
(2) the monoclonal antibody AT270 produced by the hybridoma deposited at the ECACC on Jul. 7, 1993 under No. 93070774;
(3) the monoclonal antibody AT8 produced by the hybridoma deposited at the ECACC on Oct. 8, 1991 under No. 91100806;

and with said mixture being preferably chosen from the following list:

- a mixture of monoclonal antibodies comprising the monoclonal antibodies (1) and (2),
- a mixture of the monoclonal antibodies comprising the monoclonal antibodies (1) and (3),
- a mixture of the monoclonal antibodies comprising the monoclonal antibodies (2) and (3),
- a mixture of the monoclonal antibodies comprising the monoclonal antibodies (1), (2) and (3);

with said method or kit being further characterized as containing or using:

- a preparation containing the sample to be diagnosed in vitro;
- a second antibody
    which can be a monoclonal antibody recognizing an epitope of abnormally phosphorylated tau protein, or an epitope of any phosphorylated tau peptide carrying an epitope, with said epitopes being different from the one of the invention, or
    which can be a polyclonal antibody recognising abnormally phosphorylated tau or a polyclonal antibody recognizing a peptide carrying an epitope of PHF-tau, with said polyclonal antibody being capable of forming an immunological complex with epitopes which are different from the epitope of the invention, with said polyclonal antibody being preferably purified by immunoaffinity chromatography using immobilized tau protein;
- a marker either for specific tagging or coupling with said second antibody;
- appropriate buffer solutions for carrying out the immunological reaction between the monoclonal antibody of the invention and a test sample on the one hand, and the bound second antibody and the marker on the other hand,
- possibly a peptide carrying an epitope of PHF-tau for standard purposes, or for competition purposes with respect to the antigen which is sought.

According to yet another preferred embodiment, the present invention relates to a method or kit for detecting or diagnosing in vitro a brain/neurological disease involving abnormally phosphorylated tau protein, such as Alzheimer's disease, which involves a sandwich ELISA detection format comprising coating and detecting antibodies with said coating antibodies consisting of at least one monoclonal antibody of the invention, and with said detecting antibodies consisting of at least one monoclonal antibody capable of detecting normal and/or abnormally phosphorylated human tau of which the epitope is different from any of the epitopes of the monoclonal antibodies of the invention. Such a preferred sandwich ELISA format is extensively illustrated in the examples section of the present invention.

TABLE AND FIGURE LEGENDS

Table 1

Detection of PHF-tau and normal tau using PHF-tau specific monoclonal antibodies AT180 and AT270. Microplates coated with saturating amounts of a monoclonal antibody specifically recognizing PHF-tau were incubated with CSF spiked with different amounts of non-phosphorylated or phosphorylated tau, the latter prepared by incubating recombinant non-phosphorylated tau with a rat brain extract capable of phosphorylating Ser and Thr amino acids at positions corresponding to the sites of abnormal phosphorylation of tau (Goedert et al., 1993). Bound antigen was detected as described in the examples section.

Table 2

CSF samples from AD patients, control patients and patients suffering from various non-AD neurological disorders were tested in ELISA using different combinations of capturing antibodies as described (example III). All values are expressed as mOD units except for the determination of total tau which was done using the Innotest htau (Innogenetics, Belgium) and which are expressed in pg/ml CSF.

The different experimental conditions used for each set-up do allow only intra-lane comparison.

Table 3

CSF samples of control patients, AD patients and patients suffering from various non-AD neurological disorders (OND) were assayed using the Innotest htau (Innogenetics. Belgium). From the cohorts of AD patients and OND patients those having high total tau values were selected for further testing using the PHF-tau specific ELISA in which AT8, AT180 and AT270 were used as capturing antibodies and AT120 and HT7 as detecting antibodies as described (Example IV). Results are expressed in pg/ml tau in CSF for total tau (Innotest htau) and as mOD units for the PHF-tau specific ELISA.

FIG. 1

Detection of PHF-tau and normal tau using monoclonal antibody AT180. Microplates coated with saturating amounts of monoclonal antibody AT180 specifically recognizing PHF-tau were incubated with CSF spiked with different amounts of non-phosphorylated or phosphorylated tau, the latter prepared by incubating recombinant non-phosphorylated tau with a rat brain extract capable of phosphorylating Ser and Thr amino acids at positions corresponding to the sites of abnormal phosphorylation of tau (Goedert et al., 1993). Bound antigen was detected as described in the examples section.

FIG. 2

Detection of PHF-tau and normal tau using monoclonal antibody AT270. Microplates coated with saturating amounts of monoclonal antibody AT270 specifically recognizing PHF-tau were incubated with CSF spiked with different amounts of non-phosphorylated or phosphorylated tau, the latter prepared by incubating recombinant non-phosphorylated tau with a rat brain extract capable of phosphorylating Ser and Thr amino acids at positions corresponding to the sites of abnormal phosphorylation of tau (Goedert et al., 1993). Bound antigen was detected as described in the examples section.

FIG. 3

Phosphorylation of wild-type and mutated recombinant tau (expressed from clone human tau 24; Goedert and Jakes, 1990) with the protein kinase activity from rat brain. Immunoblots with anti-tau antiserum 134 and monoclonal antibodies AT8 and AT180. Lanes 1. tau 24; 2, tau 24 plus brain extract; 3, T231 A tau 24; 4, T231 A tau 24 plus brain extract. 5, S235 A tau 24; 6, S235 A tau 24 plus brain extract.

FIG. 4

Phosphorylation of wild-type and mutated recombinant tau (expressed from clone human tau 24) with the protein kinase activity from rat brain. Immunoblots with anti-tau antiserum 134 and monoclonal antibodies AT8 and AT270.

Lanes 1, tau 24; 2, tau 24 plus brain extract; 3, T175 A tau 24; 4, T175 A tau 24 plus brain extract; 5, T181 A tau 24; 6, T181A tau 24 plus brain extract.

EXAMPLES

Example I

Preparation of the Monoclonal Antibodies AT180 and AT270 Using PHF-tau as Antigen 1. Preparation of the Antigen for Immunization PHF-tau was partially purified by a modification of the method of Greenberg and Davies (1990). Postmortem tissue, consisting mostly of gray matter from the frontal and temporal cortex, was obtained from histologically confirmed Alzheimer patients. This Alzheimer gray matter brain sample (5–10 g) was homogenized with 10 volumes of cold buffer H (10 mM Tris/1 mM EGTA/0.8 M NaCl/10% sucrose, pH 7.4) in a Teflon/glass Potter S (Braun, Germany) homogenizer. After centrifugation of the homogenate in a 60 Ti MSE rotor at 27.000×g for 20 min at 4° C., the pellet was removed and the supernatant was adjusted to 1% (wt/vol) N-laurosylsarcosine and 1% (vol/vol) 2-mercaptoethanol and incubated while rotating on a mixer (Swelab, Sweden) for 2.5 hours at 37° C. The supernatant mixture was centrifuged at 108,000×g for 35 min at 20° C. The PHF-tau containing pellet was gently washed with PBS and finally suspended in 1 ml of the same buffer.

The antigen preparation was evaluated by a 10% sodium dodecyl sulfate-polyacrylamide gel electrophoresis, followed by Western blotting using polyclonal rabbit anti-human normal tau antiserum (Mercken et al., 1992a).

2. Immunization Protocol and Fusion Procedure

Balb/c mice were primed subcutaneously with 100 μg PHF-tau preparation in complete Freund's adjuvant and boosted intraperitoneally 3 times thereafter at 3-week intervals with 100 μg of the same antigen in incomplete Freund's adjuvant. On days 3 and 2 before the fusion, mice were boosted with 100 μg to PHF-tau in saline.

Mouse spleen cells were fused with SP2/0 myeloma cells, using a modified procedure of Köhler and Milstein (1975), with PEG 4000.

The cells of the fusion experiment were suspended at a density of $4.5 \times 10^4$ spleen cells/well on 96-well plates pre-seeded with mouse peritoneal macrophage cells as a feeder layer. These wells were screened after 12 days of continuous growth for anti-PHF-tau antibody production by means of a sandwich ELISA as detailed below.

Hybridoma growth was performed in Dulbecco's modified Eagle's medium (DMEM) supplemented with 20% fetal calf serum, sodium pyruvate (1 mM), L-glutamine (2 mM), penicillin (100 U/ml), streptomycin (100 mg/ml), and non-essential amino acids. All products were purchased from Gibco, (Paisley, U.K.). Cells were incubated in a humidified $CO_2$-air incubator.

3. Sandwich ELISA for Anti-PHF-tau Antibody Screening

The screening ELISA used for the detection of anti-PHF-tau monoclonal antibodies was a sandwich ELISA system with affinity-purified polyclonal rabbit anti-human tau antibodies (Mercken et al., 1992a) in the coating phase. To this end, purified human normal tau, prepared as described in Mercken et al. (1992a) was used for the preparation of an immuno-affinity column using covalent immobilization on cyanogen bromide-activated Sepharose (Pharmacia, LKB Sweden). The affinity-bound anti-tau fraction was eluted from this column with a 0.1 M citric acid buffered solution at pH 2.5. After neutralization, the anti-tau-containing fractions were pooled and coated overnight (1 μg/ml) at 4° C. on high-binding microtiter plates (Nunc, Gibco, Paisley, UK) in coating buffer (10 mM Tris, 10 mM NaCl, 10 mM NaN$_3$, pH 8.5). After overcoating for 30 min with 125 µl 10%-saturated casein in PBS to reduce non-specific binding, the plates were incubated with 100 µl of an appropriately diluted PHF-tau preparation and incubated for 60 min at 37° C. The plates were washed 3 times with PBS-0.05% Tween 20 (v/v); 100 µl hybridoma supernatant was added and incubation was continued for 1 h at 37° C. After washing, the bound monoclonal antibodies were detected with peroxidase-conjugated rabbit anti-mouse serum (Dakopatts, Glostrup, Denmark). All reagents were diluted in PBS with 10% casein. After final washing, 100 µl 0.42 mM 3,5,3',5'-tetramethylbenzidine, 0.003% H$_2$O$_2$ v/v in 100 mM citric acid, 100 mM disodium hydrogen phosphate, pH 4.3, was added as peroxidase substrate. The reaction was stopped with 50 µl of a 2 M H$_2$SO$_4$ solution. Absorbance was read in a Titertek Multiscan (Flow Laboratories, Eflab, Oy, Finland) at 450 nm.

From such a fusion experiment, using the screening procedure as described in section 3 above, 28 positive cultures (i.e. anti-PHF-tau monoclonal antibodies secreting cultures) were retrieved out of a total of 1440 cultures. These positive cultures were arbitrarily designated AT1 to AT28 (some of these hybridoma cultures, i.e. AT1 to AT14 are described by Mercken et al., 1992b). As in this initial screening round positive cultures were mostly found to be composed of mixed clones as seen by visual inspection of the wells (usually between 1 and 4 clones per well). All hybridoma cultures were further subcloned by limiting dilution, a technique well known to those skilled in the art, finally resulting in pure hybridoma clones secreting antibodies with a homogeneous idiotype. Some of these pure hybridoma clones were further tested with respect to their reactivity patterns on normal and PHF-tau in ELISA as described in Example II and the location of their epitopes by means of Western blot analysis using tau mutants as disclosed in Example II.

The latter procedure was carried out as follows: Purified normal human tau and PHF-tau were applied to 10% SDS-polyacrylamide gels and run under denaturing conditions according to Laemmli (1970).

After SDS-PAGE, the transfer to nitrocellulose (Hybond-C, Amersham, Brussels, Belgium) was carried out in 10 mM NaHCO3, 3 mM Na2CO3, pH 9.9 for 120 min at 55 V with cooling. After blotting, the nitrocellulose was equilibrated to phosphate buffered saline (PBS), and protein binding sites were blocked with blot buffer (PBS supplemented with 5% w/v skimmed dried milk and 10% v/v newborn calf serum). Blotted proteins were incubated overnight at 4° C. with the antibody of the respective hybridoma. After three washings with PBS-0.05% Tween 20 (v/v), horseradish peroxidase-labeled rabbit anti-mouse immunoglobulins (Dakopatts, Glostrup. Denmark) were used at a dilution of 1/3000 and were incubated for 90 min at room temperature. All antisera were diluted in blot buffer. The blots were then washed three times in PBS/Tween and developed with substrate solution (PBS, 0.05% w/v 3,3'-diaminobenzidine. 0.03% v/v H2O2) after which the reaction was stopped in H2O.

As a result of these analyses, 8 hybridomas out of 28 (including AT180 and AT270) were found to be truly PHF-tau specific. These PHF-tau specific monoclonal antibodies were finally tested for their detection capacity of PHF-tau in cerebrospinal fluid using an ELISA (as illustrated in Example IV). As is illustrated in the further examples, two monoclonal antibodies, referred to as AT270 and AT180, could be found which allowed the specific detection of at least than 10 pg/ml phosphorylated tau as determined in CSF spiked with different amounts of phosphorylated and non-phosphorylated tau without applying amplification techniques (phosphorylated tau was prepared by incubating recombinant non-phosphorylated tau with a rat brain extract capable of phosphorylating Ser and Thr amino acids at positions corresponding to the sites of abnormal phosphorylation of tau as described in Goedert et al., 1993). Moreover, the monoclonal antibody AT270 was capable of detecting PHF-tau in unconcentrated CSF (see further). An assay based on the use of AT180 allowed to detect PHF-tau in 5-fold concentrated CSF, while AT8 was not capable to detect PHF-tau in 10-fold concentrated CSF. Based on these criteria, the hybridomas AT180 and AT270 were selected for further characterization of their epitopes and deposited at the ECACC under numbers 92122104 and 93070774.

4. Determination of the Antibody Class and Subclass

The antibody class and subclass was determined by Inno-LIA (Innogenetics, Ghent, Belgium). The antibodies AT180 and AT270 appeared to be of the IgG1, kappa subtypes.

Example II

Characterization of PHF-tau Specific Antibodies and Their Epitopes

1. Discrimination of Abnormally Phosphorylated tau from Normal tau in ELISA

The preparation of affinity purified normal tau is described in Mercken et al. (1992b) and for PHF-tau is essentially as described in Greenberg and Davies (1990); Mercken et al. (1992a). Purity of normal tau and PHF-tau standards was determined by SDS-PAGE. The samples were also analyzed on 420 A/H amino acid analyzer (Applied Biosystems B. V., Maarssen, The Netherlands) according to the manufacturer's instructions. Both normal and PHF-tau showed the expected amino acid compositions. The exact protein concentration of both affinity purified normal and PHF-tau was determined using an internal standard peptide.

PHF-tau monoclonal antibodies derived from the hybridomas AT180 or AT270 and purified from serum-free conditioned medium by Protein G column chromatography, were coated overnight at 4° C. on high-binding microtiter plates (Nunc, Gibco, Paisley, UK) in coating buffer at 3 µg/ml (10 mM Tris, 10 mM NaCl, 10 mM NaN$_3$, pH 8.5). After overcoating for 30 min with 150 µl 10%-saturated casein in PBS to reduce non-specific binding, the plates were incubated with 100 µl of an appropriately diluted tau or PHF-tau standard and incubated for 60 min at 37° C. The plates were washed 5 times with PBS-0.05% Tween 20 (v/v) and 100 µl of two biotinylated antibodies (AT120 and HT7, Vandermeeren et al., 1993; Mercken, Ph. D. thesis) at a final concentration of 0.2 µg/ml was added and incubated for 1 hr at room temperature. After washing horse-radish peroxidase conjugated streptavidine (Jackson, Innogenetics, Belgium) at a dilution of 1/10000 was added for 30 min at room temperature. Following a final washing with PBS/Tween 20, 100 µl of 0.42 mM 3,5,3',5'-tetramethylbenzidine, 0.003% (vol/vol) H$_2$O$_2$ in 100 mM citric acid, 100 mM Na$_2$HPO$_4$, pH 4.3 were added as peroxidase substrate for 30 min at room temperature. The reaction was stopped with 50 µl of a 2 M H$_2$SO$_4$ solution. Absorbance was read in a Titertek Multiscan (Flow Laboratories, Eflab Oy, Finland) at 450 nm.

Figure 1:
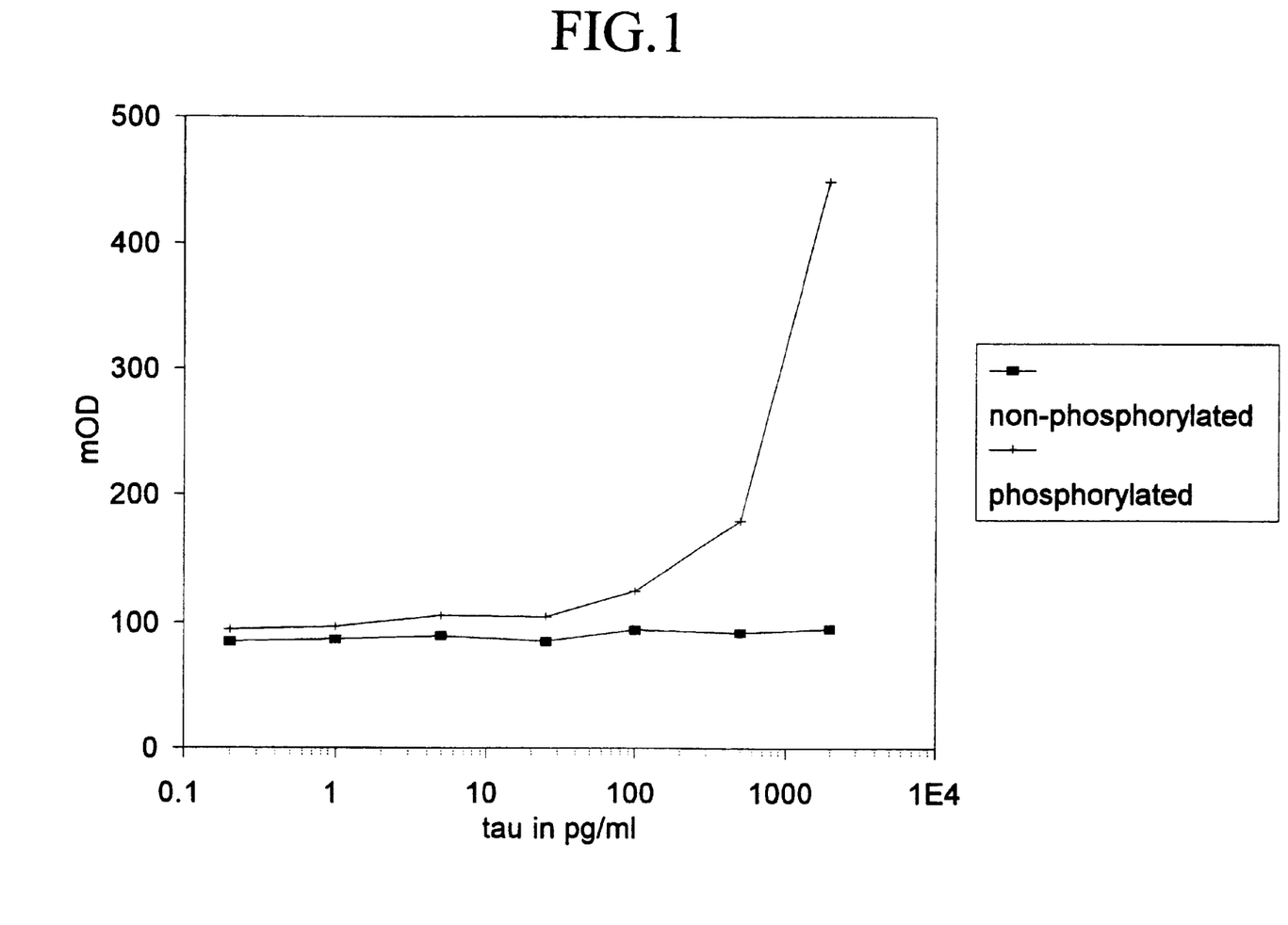
Figure 2:
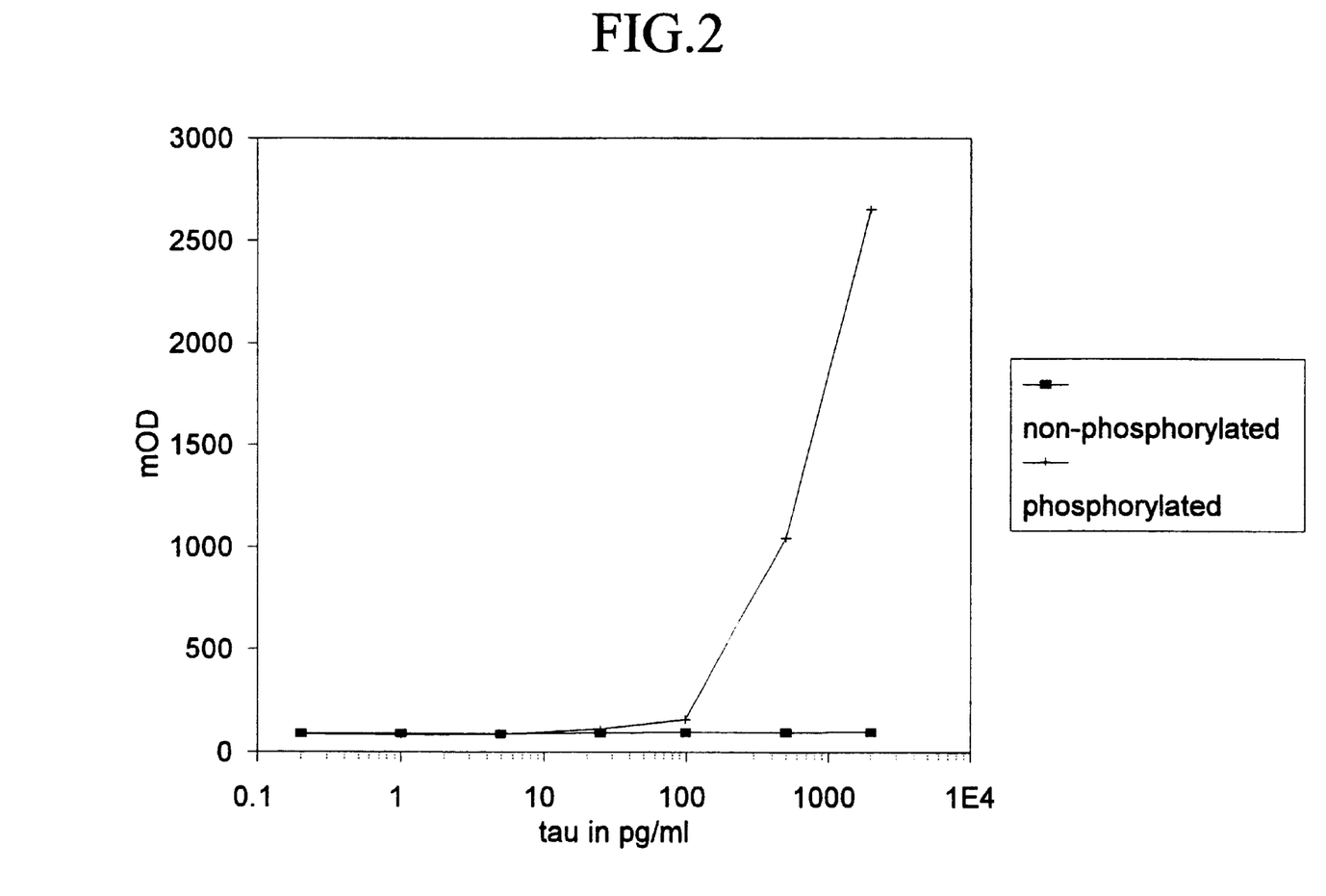

The specificity of AT180 and AT270 for PHF-tau is shown (Table 1, FIGS. 1 and 2) from which it can be seen that even at 1 µg normal tau no reactivity is present.

2. Mapping of the Epitope of the Selected PHF-tau Specific Antibodies via Recombinant tau Mutants A full-length cDNA clone (human tau 24; htau24) corresponding to a four repeat isoform of tau and with an NdeI site in the context of the inititiator codon (Goedert and Jakes, 1990) was subcloned into the EcoRI site of M13mpl8. Site-directed mutagenesis was used to change the codons representing the following amino acids to an Ala: T153, T175, T181, T199, T205, T212, T217, T231, S235, further referred to as T153A etc. mutants. Constructs containing combinations of these sites were also evaluated. Following cleavage with NdeI and EcoRI the resulting fragments were subcloned downstream of the T7 RNA polymerase promoter in the expression plasmid pRK172 (Mc Leod et al., 1987) and the recombinant plasmids were transformed into E. coli BL21(DE3) (Studier et al., 1990) cells. The bacterial cultures were grown, induced and tau proteins purified as described (Goedert and Jakes, 1990).

The brain protein kinase activity was prepared by homogenizing adult rat brain (1 g/2.5 ml) in 10 mM okadaic acid, 1 mM PMSF, 20 μg/ml leupeptin, 20 μg/ml aprotinin and 20 μg/ml pepstatin and centrifuged at 40,000 rpm for 1 h at 4° C. The supernatant was used directly for phosphorylation (Goedert et al., 1993). Incubations (0.05 ml) were carried out at 37° C. and comprised 40 mM HEPES, pH 7.2, 2 mM ATP, 2 mM $MgCl_2$, tau protein (1 μM). rat brain extract (1 μl), 5 mM EGTA, 2 mM DTT, 1 μM okadaic acid, 1 mM PMSF, 20 μg/ml aprotinin and 20 μg/ml pepstatin. Reactions were initiated by addition of the brain extract. incubated for 24 h and aliquots used for SDS-PAGE. Controls were incubated under the same conditions, except that the brain extract was omitted.

Results

Figure 3:
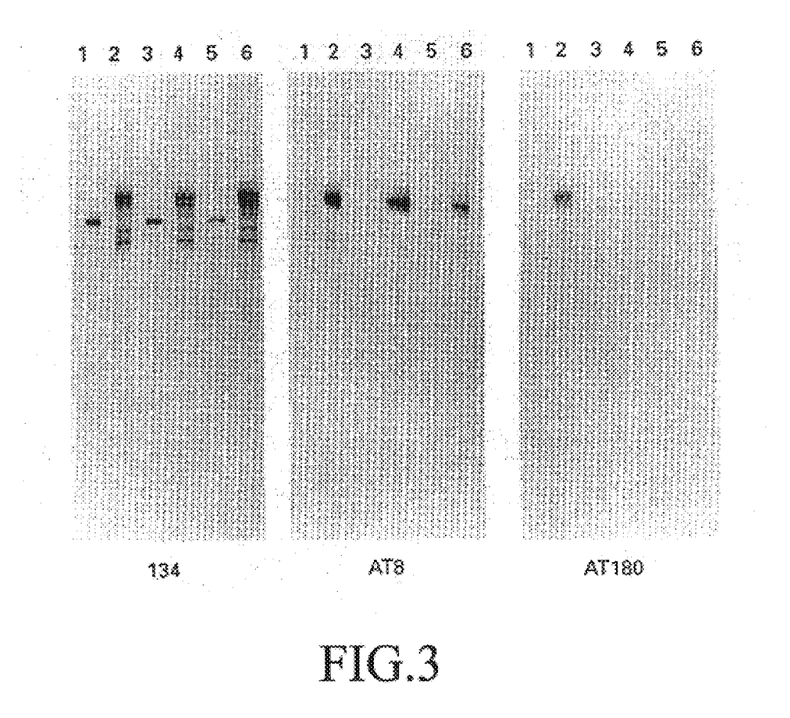
Figure 4:
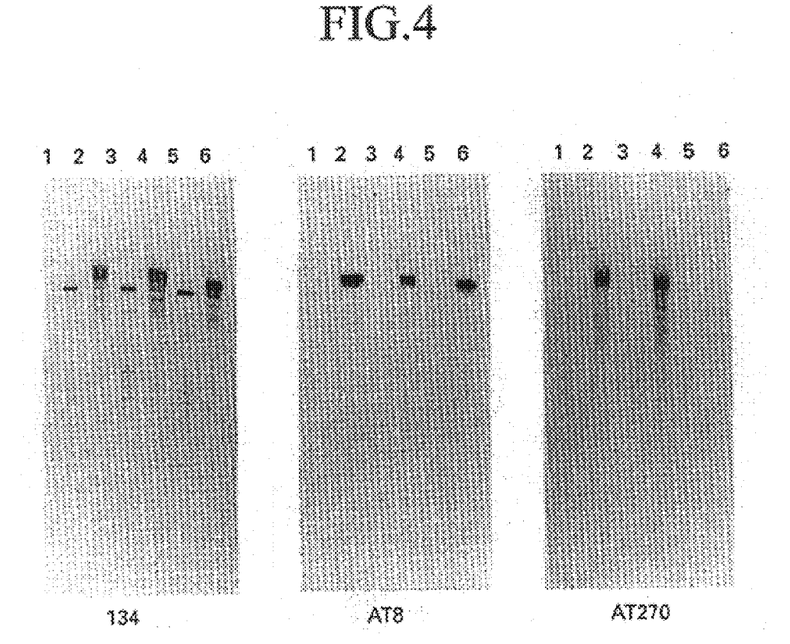

The normal htau24 clone or htau24 mutants were phosphorylated by a protein kinase containing rat brain extract (Goedert et al, 1993), run on SDS-PAGE and immunoblotted using AT180, AT270 or a tau antiserum, 134, that is phosphorylation independent (Goedert et al, 1989). AT270 and AT180 did not stain wild-type or mutant tau proteins prior to brain extract phosphorylation. However after a 24 h incubation with brain extract, AT270 recognized wild-type tau, but not T181A tau (FIG. 3). This establishes that staining by AT270 minimally requires T181 to be phosphorylated. Monoclonal antibody AT180 did equally recognize the phosphorylated wild-type tau but failed to recognize the phosphorylated T231A mutant, indicating that the AT180 epitope needs T231 phosphorylation for recognition (FIG. 4). The rather weak staining on the S235A mutant is due to the fact that some factors in the brain extract are limiting in this type of assay and consequently the S235 site was not always fully converted to its phosphorylated state, as was confirmed by using activated recombinant protein kinases as phoshorylating agents (data not shown). When recombinant tau was treated with activated recombinant MAP kinase alone or GSK3 kinase alone the AT180 epitope could not be produced, while the same experiment performed with a mixture of MAP kinase and GSK3 kinase allowed correct phosphorylation and immunoreactivity with AT180.

Example III

Using Different Combinations of the PHF-tau Antibodies to Detect PHF-tau in Unconcentrated CSF We have previously shown that an assay to detect abnormally phosphorylated tau based on the sole use of AT8 antibody as detector is not capable of detecting the AT8 epitope nor in unconcentrated nor in concentrated CSF (Vandermeeren et al, 1993). Continuing experiments with AT180 and AT270 show that the epitope of AT270 present on abnormally phosphorylated tau can be detected in most unconcentrated Alzheimer CSF samples, whereas the AT180 epitope only detects abnormally phosphorylated tau in those CSF samples containing high total tau levels and thus does not detect PHF-tau in all Alzheimer CSF samples. We subsequently used AT270 alone or in different combinations with other antibodies (AT8, AT180). Combinations of antibodies were used as solid phase bound coating antibodies to look for the presence of PHF-tau in CSF of patients suffering from different neurological disorders in which abnormally phosphorylated tau has been described, such as Pick's disease, Creutzfeld-Jacob disease, and Parkinson's disease (see Table 2).

A preferred PHF-tau specific assay can be as follows: coating of the three monoclonal antibodies, AT8, AT180, AT270 at a final concentration of 5 μg/ml in 10 mM Tris pH 8.6, 10 mM NaCl, 10 mM NaAz overnight at 4° C. on high-binding microtiter plates (Nunc, GIBCO, Paisley. U.K.). After overcoating for I hr with 150 μl of 10% satured casein in phosphate-buffered saline (PBS) to reduce non-specific binding, the plates were incubated with 100 μl of an appropriately diluted recombinant phosphorylated tau standard, or with unconcentrated CSF samples, supplemented with 5% Tween 20, overnight at room temperature. The plates were washed five times with PBS/0.05% Tween 20 (vol/vol), and 100 μl of two biotinylated antibodies (AT120 and HT7; Vandermeeren et al., 1993; Mercken, Ph. D. thesis) at a final concentration of 0.2 μg/ml was added and incubated for 1 hr at room temperature. After washing, horse-radish peroxidase conjugated streptavidine (Jackson. Innogenetics. Belgium) at a dilution of 1/10000 was added for 30 min at room temperature. Following a final washing with PBS/Tween 20. 100 μl of 0.42 mM 3,5,3',5'-tetramethylbenzidine, 0.003% (vol/vol) $H_2O_2$ in 100 mM citric acid, 100 mM $Na_2HPO_4$, pH 4.3 were added as peroxidase substrate for 30 min at room temperature. The reaction was stopped with 50 μl of a 2 M $H_2SO_4$ solution. Absorbance was read in a Titertek Multiscan (Flow Laboratories. Eflab Oy, Finland) at 450 nm.

Example IV

Detection of PHF-tau in Cerebrospinal Fluid Samples with the Selected PHF-tau Specific Monoclonal Antibodies Cerebrospinal Fluid Samples Antemortem CSF samples from patients were collected at the department of Neurology of the University Hospital of Antwerp. All samples were obtained by lumbar puncture performed for routine diagnostic purposes. CSF samples were frozen and kept at −70° C. until use. Samples were taken from Alzheimer patients, from patients with no neurological complications and from patients with various neurological disorders. Those samples were assayed for total tau concentration using the Innotest htau (Innogenetics, Belgium) and samples having high total tau values were retained for further analysis for the presence of PHF-tau with the preferred PHF-tau assay as specified in Example 111.

Results

Using this assay and the CSF samples as described, the results summarized in Table 3 were obtained. From this, it is obvious that the mean PHF-tau levels remain rather low for controls and OND patients (controls: 381 mOD; OND, degenerative: 423 mOD; OND, inflammatory: 392 mOD; OND, vascular: 340 mOD), while the mean for Alzheimer patients is 814 mOD units. Furthermore, as can be seen in Table 3, high total tau values in the OND group are not always reflected by a parallel increase in PHF-tau while in the AD patients high total tau levels always give rise to increased concentrations of PHF-tau. The accumulated evidence from the control group, the OND cohorts and the AD patients therefore strongly points to the diagnostic specificity of the PHF-tau assay for AD and AD-related syndromes (such as multiple infarct dementia, Parkinson's disease mixed dementia and one unspecified dementia).

TABLE 1

| tau pg/ml | AT180 non-phosphorylated | AT180 Phosphorylated | AT270 non-phosphorylated | AT270 Phosphorylated |
|---|---|---|---|---|
| 2000 | 95 | 449 | 98 | 2653 |
| 500 | 92 | 179 | 94 | 1044 |
| 100 | 94 | 125 | 96 | 158 |
| 25 | 85 | 105 | 92 | 113 |
| 5 | 90 | 106 | 87 | 86 |
| 1 | 87 | 97 | 90 | 83 |
| 0.2 | 85 | 95 | 91 | 89 |
| 0 | 89 | 94 | 92 | 94 |

TABLE 2

| Nr | Diagnosis | tau in pg/ml | AT270 in mOD | AT180,270 in mOD | AT8,270 in mOD | AT8,180,270 in mOD |
|---|---|---|---|---|---|---|
| 3 | AD (early onset) | 56.5 | 185 | 613 | 126 | 916 |
| 5 | AD | 62 | 132 | 410 | 105 | 636 |
| 6 | AD | 71 | 107 | 310 | 87 | 678 |
| 38 | AD | 68.7 | 257 | 685 | 169 | 1251 |
| 73 | AD | 27.7 | 84 | 96 | 44 | 570 |
| 88 | AD | 25.3 | 124 | 261 | 68 | 705 |
| 276 | AD | 43 | 106 | 325 | 76 | 612 |
| 281 | AD | 46 | 184 | 406 | 100 | 199 |
| 874 | AD | 51 | 128 | 353 | 88 | 777 |
| 61 | Control | 17.3 | 53 | 80 | 87 | |
| 1435 | Hydrocephalus | 18 | 62 | 38 | 53 | 297 |
| 401 | Control | 20.1 | 77 | 73 | 53 | |
| 242 | PNP | 20.8 | 109 | 169 | 77 | 276 |
| 1424 | Control | 21 | 96 | 79 | 61 | 304 |
| 85 | Control | 22 | 54 | 52 | 43 | 83 |
| 153 | CNS lymphoma | 22.2 | 55 | 111 | 47 | 301 |
| 1337 | Hydrocephalus | 29 | 45 | 68 | 47 | 124 |
| 1337 | Hydrocephalus | 29 | 43 | 75 | 45 | 124 |
| 1381 | NPH | 32 | 78 | 156 | 75 | 366 |
| 1470 | NPH | 33 | 77 | 152 | 60 | 148 |
| 641 | Control | 35 | 64 | 135 | 67 | 515 |
| 349 | Meningitis | 35.6 | 76 | 95 | 68 | 367 |
| 109 | Pick | 40.5 | 89 | 131 | 60 | 398 |
| 1467 | Pseudotumor | 44 | 111 | 149 | 64 | 373 |
| 193 | GBS | 44.1 | 158 | 238 | 107 | 295 |
| 114 | Cerebell Atro. | 51.5 | 90 | 97 | 56 | 203 |
| 130 | External aftalmophlegia | 53.6 | 102 | 99 | 60 | 229 |
| 131 | Meningeal bleeding | 66.7 | 65 | 82 | 49 | 338 |
| 214 | CJD | 92 | 82 | 204 | 70 | 387 |
| 53 | PD | 57 | 249 | 682 | 137 | 836 |
| 150 | Control | 79 | 284 | 848 | 207 | 1557 |
| 137 | Pick | 77.4 | 423 | 987 | 220 | 1571 |

TABLE 3

| Nr | Sex | Age | Diagnosis | tau (pg/ml) | PHF-tau (in mOD) |
|---|---|---|---|---|---|
| Alzheimer patients | | | | | |
| 304 | F | | AD (= Alz21) | 86 | 517 |
| 3 | F | ? | AD (early onset) | 56.5 | 916 |
| 874 | F | 42 | AD | 51 | 777 |
| 113 | F | 44 | AD | 42.6 | 627 |
| 1085 | M | 46 | AD | 543 | 3049 |
| 265 | F | 47 | AD (?) | 62 | 441 |
| 161 | F | 57 | AD, Creutzfeld-Jacob(?) | 33.8 | 682 |
| 326 | F | 58 | AD | 34 | 394 |
| 1499 | F | 60 | AD | 147 | 1425 |
| 220 | M | 60 | AD | 126 | 1614 |
| 6 | M | 61 | AD | 71 | 678 |
| 718 | M | 62 | AD | 53 | 588 |
| 335 | F | 63 | AD, probable | 83 | 656 |
| 720 | M | 64 | AD | 170 | 1573 |
| 174 | F | 64 | AD | 66 | 609 |
| 338 | F | 64 | AD | 51.2 | 593 |
| 262 | F | 65 | AD | 221 | 2224 |
| 254 | F | 66 | AD | 80.2 | 923 |
| 73 | M | 67 | AD | 27.7 | 570 |
| 209 | M | 67 | AD | 74.4 | 1341 |
| 722 | M | 67 | AD | 71 | 433 |
| 383 | M | 67 | AD | 32.5 | 691 |
| 38 | M | 67 | AD | 68.7 | 1251 |
| 1259 | F | 68 | AD (?) | 65 | 698 |
| 723 | M | 69 | AD | 54 | 614 |
| 721 | M | 70 | AD | 99 | 947 |
| 17 | F | 70 | AD | 37 | 582 |

TABLE 3-continued

| Nr | Sex | Age | Diagnosis | tau (pg/ml) | PHF-tau (in mOD) |
|---|---|---|---|---|---|
| 1 | F | 72 | AD + MS | 33 | 222 |
| 229 | M | 73 | AD | 70.9 | 1043 |
| 278 | F | 75 | AD | 54 | 1069 |
| 719 | M | 75 | AD | 70 | 884 |
| 88 | F | 76 | AD | 25.3 | 705 |
| 132 | F | 76 | AD | 51.9 | 1187 |
| 65 | F | 77 | AD | 80.1 | 1284 |
| 287 | M | 78 | AD (?) | 58 | 423 |
| 737 | F | 78 | AD | 43 | 330 |
| 71 | F | 78 | AD | 53.9 | 741 |
| 28 | M | 78 | AD | 48.7 | 476 |
| 760 | F | 78 | AD | 36 | 299 |
| 5 | M | 81 | AD | 62 | 636 |
| 281 | F | 81 | AD | 46 | 199 |
| 13 | F | 81 | AD | 13 | 179 |
| 289 | M | 83 | AD | 29 | 502 |
| 96 | F | 84 | Steele-Richardson (?), AD (?) | 41 | 295 |
| 223 | M | 84 | AD | 52 | 487 |
| 185 | F | 85 | AD | 59 | 724 |
| 276 | F | 85 | AD | 43 | 612 |
| 39 | F | 86 | AD | 150 | 2205 |
| 343 | F | 86 | AD (?) | 44 | 413 |
| 14 | F | 86 | AD | 57 | 825 |
| 606 | F | 86 | AD | 43 | 680 |
| 724 | M | 88 | AD | 31 | 487 |
| | | | Control patients | | |
| 145 | F | 40 | | 31.9 | 363 |
| | F | 68 | | 39 | 436 |
| | F | 72 | | 84 | 718 |
| 709 | F | 56 | | 29 | 259 |
| 1508 | M | 64 | | 21 | 155 |
| 1100 | M | 71 | | 31 | 313 |
| 1424 | M | 64 | | 21 | 304 |
| | F | 66 | | 35 | 515 |
| | F | 77 | | 43.5 | 447 |
| 544 | M | 69 | | 17 | 304 |
| | | | Other Neurological Disorders, Degenerative types | | |
| 196 | F | 71 | Parkinson + dementia | 84 | 421 |
| 167 | M | 61 | cerebellum atrophy | 14 | 433 |
| 75 | M | 71 | alcohol induced dementia | 26 | 763 |
| 53 | F | 69 | Mixed dementia, Parkinson | 55 | 589 |
| 53 | F | 85 | Parkinson, mixed dementia | 59.3 | 1083 |
| 137 | F | 57 | Pick's disease | 77.4 | 1571 |
| 946 | F | 75 | cortical atrophy, periventricular | 57 | 814 |
| 713 | F | 48 | FLD | 39 | 341 |
| 186 | M | 66 | ALS | 21.2 | 208 |
| 344 | F | 68 | Parkinson dementia | 28 | 205 |
| 22 | F | 65 | Steele Richardson | 13 | 203 |
| 114 | M | 51 | atrophy cerebellum | 51.5 | 203 |
| 334 | M | 57 | Parkinson, dyskinesia | 22 | 218 |
| 1527 | M | 61 | Parkinson + syphilis | 17 | 277 |
| 772 | F | 70 | Steele-Richardson | 26 | 244 |
| 169 | F | 27 | Dementia (?) | 37.5 | 337 |
| 794 | F | 61 | Steele-Richardson | 24 | 149 |
| 214 | F | 59 | Creutzfeld-Jacob | 292 | 387 |
| 109 | M | 63 | Pick; ALS | 40.5 | 398 |
| 33 | M | 63 | Pick | 61 | 395 |
| 230 | F | 66 | Parkinson | 21.1 | 157 |
| | | | Other Neurodegenerative diseases, inflammatory types | | |
| 668 | F | 79 | encephalitis | 16 | 282 |
| 673 | F | 72 | encephalitis | 16 | 281 |
| 710 | F | 28 | MS | 14 | 186 |
| 405 | M | 29 | Guillain-Barré (GBS) | 47.6 | 278 |
| 1396 | M | 67 | ALS | 150 | 289 |
| 1261 | M | 28 | CIDP | 24 | 293 |
| 193 | M | 68 | GBS | 44.1 | 295 |
| 279 | F | 70 | M.S. | 17 | 113 |
| 314 | F | 69 | GBS | 34 | 292 |
| 716 | M | 54 | ALS | 15 | 220 |
| 1477 | M | 67 | ALS | 150 | 797 |
| 717 | M | 53 | ALS | 18 | 158 |
| 163 | M | 71 | Meningitis | 150 | 1891 |
| 93 | M | 85 | polyneuropathy | 61.9 | 764 |
| 327 | F | 66 | ALS | 20 | 127 |
| 708 | M | 33 | Neurocystercosis | 20 | 249 |
| 149 | M | 56 | Syphilis | 4 | 176 |
| 1493 | M | 22 | SSPE | 18 | 236 |
| 207 | M | 50 | Guillain-Barré | 70.3 | 466 |
| 706 | F | 75 | GBS | 21 | 309 |
| 64 | M | 58 | MS | 40.7 | 512 |
| 1447 | F | 58 | ALS | 38 | 340 |
| 360 | M | 54 | Lyme disease | 34.7 | 515 |
| 532 | M | 64 | TBC | 28 | 470 |
| 7 | M | 17 | SSPE | 48.1 | 403 |
| 363 | F | 47 | encephalitis | 35.9 | 424 |
| 133 | M | 24 | MS | 37.1 | 397 |
| 208 | M | 68 | polyneuropathy | 28.8 | 325 |
| 398 | M | 58 | meningoencephalitis | 117.8 | 367 |
| 715 | F | 63 | ALS | 40 | 333 |
| | | | Other Neurological diseases, vascular types | | |
| 131 | F | 59 | meningeal bleeding | 66.7 | 338 |
| 219 | F | 58 | Pseudobullar synd. | 39.6 | 231 |
| 101 | M | 55 | infarct | 52.8 | 352 |
| 228 | M | 22 | ischemic cerebral infarct | 150 | 392 |
| 294 | F | 71 | CVA, diabetes, epilepsia | 54 | 347 |
| 409 | M | 65 | multiple vascular pathology | 208 | 222 |
| 1492 | M | 47 | infarct, occip. | 69 | 213 |
| 712 | F | 44 | Seizure-new onset | 14 | 309 |
| 21 | M | 70 | congofilic angiopathy | 15 | 322 |
| 457 | M | 68 | infarct | 24 | 280 |
| 42 | M | 78 | multi-infarct dementia | 38.9 | 614 |
| 320 | M | 76 | diabetes, MID | 27 | 318 |
| 714 | M | 82 | MID | 29 | 286 |
| 98 | F | 68 | TIA | 34.9 | 577 |
| 23 | F | 82 | dementia | 31 | 303 |
| | | | Other neurological disorders, not defined | | |
| 115 | M | 68 | subacute degeneration | 14 | 561 |
| 419 | M | 1 | hydrocephalus | 150 | 2765 |
| 275 | M | 66 | PNP | 19 | 448 |
| 226 | F | 54 | progress. pyr. affliction | 18 | 445 |
| 111 | M | 67 | Polyneuropathy | 64.2 | 549 |
| 91 | F | 81 | PNP | 31.2 | 355 |
| 1467 | M | 43 | Pseudotumor | 44 | 373 |
| 153 | F | 62 | CNS lymphoma | 22.2 | 301 |
| 1435 | M | 65 | trauma hydroceph | 18 | 297 |
| 150 | F | 82 | mental disturbance | 79 | 1557 |
| 274 | M | 78 | cervical medullopathy | 69 | 160 |
| 1454 | M | 73 | hydrocephalus | 30 | 124 |
| 268 | M | 63 | PNP, alcohol | 23 | 500 |
| 711 | F | 31 | Pseudotumor cerebri | 16 | 234 |
| 170 | M | 66 | Temp. E | 24.2 | 632 |
| 195 | F | 64 | E. dialysis | 14 | 239 |
| 242 | M | 72 | polyneuropathy | 20.8 | 276 |
| 330 | M | 69 | pyr?? | 14 | 246 |
| 1478 | M | 43 | Pseudotumor | 42 | 337 |
| 1364 | M | 65 | stenosis | 32 | 475 |
| 152 | F | 66 | medullar | 33 | 450 |
| 438 | M | 71 | polyneuropathy | 34 | 205 |
| 1087 | F | 65 | stenosis | 24 | 1086 |
| 251 | F | 77 | trauma cerebri commoti | 14 | 209 |
| 1576 | F | 70 | korsakoff syndrome | 82 | 863 |
| 312 | M | 72 | meta adeno ?? | 37 | 471 |
| 1442 | F | 70 | gait disturbance | 39 | 615 |

REFERENCES

Andreadis A, Brown W, Kosik K (1992) Structure and novel exons of the human tau gene. Biochem 31:10626–10633.

Bramblett G, Trojanowski J, Lee V (1992) Regions with abundant neurofibrillary pathology in human brain exhibit a selective reduction in levels of binding-competent tau and accumulation of abnormal tau isoforms (A68 proteins). Lab Invest 66:212–222.

Bramblett G, Goedert M, Jakes R, Merrick S, Trojanowski J, Lee V (1993) The abnoramal phosphorylation of tau at Ser396 in Alzheimer's disease recapitulates phosphorylation during development and contributes to reduced microtubule binding. Neuron 10:1089–1099.

Brion J, Couck A, Passareiro E, Flament-Durand J (1985a) Neurofibrillary tangles of Alzheimer's disease: an immunohistochemical study. J Submicrosc Cytol 17:89–96.

Brion J, Passareiro J, Nunez J and Flament-Durand J (1985) Mise en evidence immunologique de la proteine tau au niveau des lesions de degenerescence neurofibrillaire de la maladie d'Alzheimer. Arch Biol 95:229–235.

Biernat J, Mandelkow M, Schoter C, Lichtenberg-Kraag B, Steiner B, Berling B, Meyer H, Mercken M, Vandermeeren M, Mandelkow E, The switch of tau protein to an Alzheimer-like state includes the phosphorylation of two serine-proline motifs upstream of the microtubule binding region. EMBO J, 1992, 11:1593–1597.

Bobrow M. Harris T, Shaughnessy K, Litt G (1989) Catalyzed reporter deposition, a novel method of signal amplification. Application to immunoassays. J Immunol Meth 125:279–285.

Butner K, Kirschner (1991) Tau protein binds to microtubules through a flexible array of distributed weak sites. J Cell Biol 115:717–730.

de Bont H, van Boom J, Liskamp R (1990a) Automatic synthesis of phosphopeptides by phosphorylation on the solid phase. Tetrahedron Letters 31:2497–2500.

de Bont H, van Boom J, Liskamp R (1990b) N,N-diiopropyl-bis(4-chlorobenzyl)phosphoramidite: A versatile phosphitylating agent for the phosphorylation of hydroxy amino acids and preparation of protected phosphopeptides. Recueil des Travaux Chimiques des Pays-bas 109:27–28.

Delacourte A, Flament S, Dibe E, Hublau P, Sablonniere B, Hemon B, Sherrer V, Defossez A (1990) Pathological proteins Tau64 and 69 are specifically expressed in the somatodendritic domain of the degenerating cortical neurons during Alzheimer's disease. Acta Neuropathol 80:111–117.

Delacourte A, Défossez A (1986) Alzheimer's disease: Tau proteins, the promoting factors of microtubule assembly, are major components of paired helical filaments. J. Neurol. Sci. 76:173–180.

Drewes G. Lichtenberg-Kraag B, Doring F, Mandelkow E-M, Biernat J, Goris J, Doree M, Mandelkow E (1992) Mitogen activated protein (MAP) kinase transforms tau protein into an Alzheimer-like state. EMBO J 11:2131–2138.

Flament S. Delacourte A, Hemon B, Defossez A (1989) Characterization of two pathological Tau protein variants in Alzheimer brain cortices. J. Neurol. Sci. 92:133–141.

Flament S, Delacourte A (1990) Tau Marker? Nature 346:6279.

Flament S, Delacourte A, Mann D (1990) Phosphorylation of tau proteins: a major event during the process of neurofibrillary degeneration. A comparitive study between Alzheimer's disease and Down's syndrome. Brain Res 516:15–19.

Ghanbari H, Kozuk T, Miller B, Riesing S (1990) A sandwich enzyme immunoassay for detecting and measuring Alzheimer's disease-associated proteins in human brain tissue. J Clin Laboratory Anal 4:189–192.

Goedert M, Jakes R (1990) Expression of seperate isoforms of human tau protein: correlation with the tau protein in brain and effects on tubulin polymerization. EMBO J 9:4225–4230.

Goedert M, Jakes R, Crowther R, Six J, Lübke U, Vandermeeren M, Cras P, Trojanowski JQ, Lee V (1993) The abnormal phosphorylation of tau protein at serine 202 in Alzheimer's disease recpitulates phosphorylation during development. Proc Natl Acad Sci (U.S.A.) 90:5066–5070.

Goedert M, Wishik C, Crowther R, Walker J, Klug A (1988) Cloning and sequencing of the cDNA encoding a core protein of the paired helical filament of Alzheimer disease: identification as the microtubuli-associated protein tau. Proc Natl Acad Sci (U.S.A.) 85:4051–4055.

Goedert M, Spillantini M, Jakes R, Rutherford D, Crowther R (1989) Multiple isoforms of human microtubule-associated protein tau: sequences and localization in neurofibrillary tangles of Alzheimer's disease. Neuron 3:519–526.

Goedert M. Spillantini M, Jakes R (1991) Localization of the Alz-50 epitope in recombinant human microtubule-associated protein tau. Neurosci Lett. 126:149–154.

Goedert M, Cohen E, Jakes R, Cohen P (1992) p42 Map kinase phosphorylation sites in microtubule-associated protein tau one dephosphorylated by protein phosphatase 2A1: implications for Alzheimer's disease. FEBS Lett. 312:95–99.

Greenberg S, Davies P (1990) A preparation of Alzheimer paired helical filaments that displays distinct tau proteins by polyacrylamide gel electrophoresis. Proc Natl Acad Sci U.S.A. 87:5827–5831.

Greenberg S, Davies P, Schein J, Binder L (1992) Hydrofluoric acid-treated tauPHF proteins display the same biochemical properties as normal tau. J Biol Chem 267:564–569.

Grundke-Iqbal I, Iqbal K, Tung Y, Quinlan M, Wisniewski H Binder L (1986) Abnormal phosphorylation of the microtubule-associated protein (tau) in Alzheimer's cytoskeletal pathology. Proc Natl Acad Sci (U.S.A.) 83:4913–4917.

Grundke-Iqbal I, Iqbal K, Quinlan M, Tung Y, Zaidi M, Wisniewski H (1986) Microtubule-associated protein tau. J Biol Chem 261:6084–6089.

Harrington C, Mukaetova E, Hills R, Edwards P, Montejo de Garcini E, Novak M, Wischik C (1991) Measurement of distinct immunochemical presentations of tau protein in Alzheimer's disease. Proc Natl Acad Sci (U.S.A.) 88:5842–5846.

Hasegawa M, Morishima-Kawashima M, Takio K, Suzuki M, Titani K, Ihara Y (1992) Protein sequence and mass spectrometric analyses of tau in Alzheimer's disease brain. J Biol Chem 267:17047–17054.

Hsu S, Raine L, Fanger H (1981) Use of avidin-biotin-peroxidase complex (ABC) in immunoperoxidase techniques: a comparison between ABC and unlabeled antibody (PAP) procedures. J Histochem Cytochem 29:577–580.

Iqbal K, Zaidi T, Thompson C, Merz P, Wisniewski H (1984) Alzheimer paired helical filaments: bulk isolation, solubility, and protein composition. Acta Neuropathol 62:167–177.

Iqbal K, Grundke-Iqbal I, Smith A, George L, Tung Y, Zaidi T (1989) Identification and localization of a Tau peptide to paired helical filaments of Alzheimer's disease. Proc Natl Acad Sci (U.S.A.) 86:5646–5650.

Ishiguro K, Takamatsu M, Tomizawa K, Omori A, Takahashi M, Arioka M, Uchida T, Imahori K (1992) Tau protein kinase I converts noraml tau protein into AA68-like component of paired helical filaments. J Biol Chem 267:10897–10901.

Kanai Y, Chen J, Hirokawa N (1992) Microtubule bundling by tau proteins in vivo: analysis of functional domains. EMBO J 11:3953–3961.

Kondo J, Honda T, Mori H, Hamada Y, Miura R, Ogawara M, Ihara Y (1988) The carboxyl third of tau is tightly bound to paired helical filaments. Neuron 1:827–834.

Kohler G, Milstein C (1975) Continuous cultures of fused cells secreting antibody of predefined specificity. Nature 256:495–497.

Kosik K, Joachim C, Selkoe (1986) Microtubule-associated protein tau is a major antigenic component of paired helical filaments in Alzheimer's disease. Proc Natl Acad Sci (U.S.A.) 83:4044–4048.

Labbe J, Cavadore J and Doree M (1991) M phase-specific cdc2 kinase: preparation from starfish oocytes and properties. Meth Enzymol 200:291–301.

Laemmli U (1970) Cleavage of structural proteins during the assembly of the head of bacteriophage T4. Nature 227:680–685.

Ledesma M, Correas I, Avila J, Diaz-Nido J (1992) Implication of brain cdc2 and MAP2 kinases in the phosphorylation of tau protein in Alzheimer's disease. FEBS Letters 308:218–224.

Lee V, Balin B, Otvos L, Trojanowski J (1991) A68: a major subunit of paired helical filaments and derivatized forms of normal tau. Science 251:675–678.

Lewis S, Wang D, Cowan N (1988) Microtubule-associated protein MAP2 shares a microtubule binding motif with Tau protein. Science 242:936–939.

Mandelkow E-M, Drewes G, Biernat J, Gustke N, Van Lint J, Vandenheede J, Mandelkow E (1992) Glycogen-synthase kinase-3 and the Alzheimer's-like state of microtubule-associated protein tau. FEBS Letters 314:315–321.

Martin J, Gheuens J, Bruyland M, Cras P, Vandenberghe A, Masters C, Beyreuther K, Dom R, Ceuterick C, Lubke U, Van Heuverswijn H, De Winter G, Van Broeckhoven C (1991) Early-onset Alzheimer's disease in 2 large Belgian families. Neurology 41:62–68.

McKahn G, Drachman D, Folstein M, Katzman R, Price D, Stadlan E (1984) Clinical diagnosis of Alzheimer's disease: report of the NINCDS-ADRA work group under the auspices of department of health and human services task force on Alzheimer's disease. Neurology 34:939–944.

Mc Leod M, Stein M, and Beach D (1987) The product of the mei3 + gene, expressed under control of the mating-type locus, induces meiosis and sporulation in fision yeast. EMBO J 6:729–736.

Mercken M, Ph. D. thesis: De neurofibrillaire degeneratie bij de ziekte van Alzheimer: een benadering met monoklonale antistoffen. Antwerp, 1991.

Mercken M, Vandermeeren M, Lubke U, Six J, Boons J, Vanmechelen E, Van de Voorde A, Gheuens J (1992a) Affinity purification of human tau proteins and the construction of a sensitive sandwich enzyme-linked immunosorbent assay for human tau detection. J Neurochem 58:548–553.

Mercken M Vandermeeren M, Lubke U, Six J, Boons J, Van de Voorde A, Martin J J. Gheuens J (1992b) Monoclonal antibodies with selective specificity for Alzheimer Tau are directed against phosphatase-sensitive epitopes. Acta Neuropathol 84:265–272.

Otvos L, Elekes 1, Lee V (1989) Solid phase synthesis of phosphopeptides. International Journal of Peptide and Protein Research 34:129–133.

Perich J (1991) Synthesis of 0-phosphoserine and O-phosphothreonine-containing peptides. Methods in Enzymology 201:225–233.

Poulter L, Barrat D, Scott C, Caputo C (1983) Localizations and immunoreactivities of phosphorylation sites on bovine and porcine tau proteins and a PHF-tau fragment. J Biol Chem 268:9636–9644.

Roder H, Ingram V (1991) Two novel kinases phosphorylate tau and the KSP site of heavy neurofilament subunits in high stoichiometric ratios. J Neurosci 11:3325–3343.

Sturgill T, Ray L, Anderson N, Erickson A (1991) Purification of activated protein kinase from epidermal growth factor treated 3T3—L1 fibroplasts. Meth Enzymol 200:342–351.

Selden S, Pollard T (1983) Phosphorylation of microtubule-associated proteins regulates their interaction with actin filaments. J Biol Chem 258(11):7064–71.

Steiner B Mandelkow E, Biernat J, Gustke N, Meyer H, Schmidt B, Mieskes G, Soling H, Drechsel D, Kirschner M, Goedert M, Mandelkow E (1990) Phophorylation of microtubule-associated protein tau: identification of the site for $Ca^{2+-}$calmodulin dependent kinase and relationship with tau phosphorylation in Alzheimer tangles. The EMBO J 9:3539–3544.

Studier F, Rosenberg A, Dunn J, Dubbendorf J (1990) Use of T7 RNA polymerase to direct expression of cloned genes. Methods Enzymol 185:60–89.

Towbin H, Staehelin T, Gordon J (1979) Electrophoretic transfer of proteins form polyacrylamide gels to nitrocellulose sheets : procedure and some applications. Proc Natl Acad Sci U.S.A. 76:4350–4354.

Vandenheede J, Yang S, Goris J, Merlevede W (1980) ATP×Mg-dependent protein phosphatase from rabbit skeletal muscle. Purification of the activating factor and its characterization as a bifunctional protein also displaying synthase kinase activity. J Biol Chem 255: 11768–11774.

Vandermeeren M, Mercken M, Vanmechelen E, Six J, Van de Voorde A, Martin J, Cras, P (1993) Detection of tau proteins in normal and Alzheimer's disease fluid with a sensitive sandwich enzyme linked assay J Neurochem 61:1828–1834.

Vulliet R. Halloran S, Braun R, Smith A, Lee, G (1992) Proline-directed phosphorylation of human tau protein. J Biol Chem 267:22570–22574.

Watanabe N, Takio K, Hasegawa M, Arai T, Titani K, Ihara Y, (1992) Tau 2: a probe for a ser conformation in the amino terminus of tau. J Neurochem 58:960–966.

Wischik C, Novak M, Edwards P, Klug A, Tichelaar W, Crowther R (1988) Structural characterization of the core of the paired helical filament of Alzheimer disease. Proc Natl Acad Sci U.S.A. 85:4884–4888.

Wolozin B, Davies P (1987) Alzheimer-related neuronal protein A68: specificity and distribution. Ann Neurol 22:521–526.

Wolozin B, Pruchnicki A, Dickson D, Davies P (1986) A neurological antigen in the brains of Alzheimer's patients. Science 232:648–650.

Wood J, Mirra S, Pollock N, Binder L (1986) Neurofibrillary tangles of Alzheimer's disease share antigenic determinants with the axonal mirotubule-associated protein tau. Proc Natl Acad Sci (U.S.A.) 83:4040–4043.

---

We claim:

1. A monoclonal antibody AT180 secreted by the hybridoma deposited at ECACC on Dec. 22, 1992 under No. 92122204, which forms an immunological complex with a phosphorylated epitope of an antigen belonging to abnormally phosphorylated tau protein (PHF-tau) residing in the region spanning positions 143–254 with the following amino acid sequence:

```
                                        (SEQ ID NO 1)
          143                          150
NH₂- Lys Gly Ala Asp Gly Lys Thr Lys Ile Ala
                          160
Thr Pro Arg Gly Ala Ala Pro Pro Gly Gln Lys Gly
                  170
Gln Ala Asn Ala Thr Arg Ile Pro Ala Lys Thr Pro
          180
Pro Ala Pro Lys Thr Pro Pro Ser Ser Gly Glu Pro
      190                              200
Pro Lys Ser Gly Asp Arg Ser Gly Tyr Ser Ser Pro
                                  210
Gly Ser Pro Gly Thr Pro Gly Ser Arg Ser Arg Thr
                          220
Pro Ser Leu Pro Thr Pro Pro Thr Arg Glu Pro Lys
              230
Lys Val Ala Val Val Arg Thr Pro Pro Lys Ser Pro
          240
Ser Ser Ala Lys Ser Arg Leu Gln Thr Ala Pro Val
     250
Pro Met Pro Asp Leu Lys COOH
``` with said monoclonal antibody specifically detecting abnormally phosphorylated tau protein (PHF-tau) in cerebrospinal fluid (CSF).

2. A hybridoma deposited at ECACC on Dec. 22, 1992 under No. 92122204, which secretes a monoclonal antibody AT 180 which forms an immunological complex with a phosphorylated epitope of an antigen belonging to abnormally phosphorylated tau protein (PHF-tau) residing in the region spanning positions 143–254 with the following amino acid sequence:

```
                                        (SEQ ID No. 1)
          143                          150
NH₂- Lys Gly Ala Asp Gly Lys Thr Lys Ile Ala
                          160
Thr Pro Arg Gly Ala Ala Pro Pro Gly Gln Lys Gly
                  170
Gln Ala Asn Ala Thr Arg Ile Pro Ala Lys Thr Pro
          180
Pro Ala Pro Lys Thr Pro Pro Ser Ser Gly Glu Pro
      190                              200
Pro Lys Ser Gly Asp Arg Ser Gly Tyr Ser Ser Pro
                                  210
Gly Ser Pro Gly Thr Pro Gly Ser Arg Ser Arg Thr
                          220
Pro Ser Leu Pro Thr Pro Pro Thr Arg Glu Pro Lys
              230
Lys Val Ala Val Val Arg Thr Pro Pro Lys Ser Pro
          240
Ser Ser Ala Lys Ser Arg Leu Gln Thr Ala Pro Val
     250
Pro Met Pro Asp Leu Lys COOH
``` with said monoclonal antibody specifically detecting abnormally phosphorylated tau protein (PHF-tau) in cerebrospinal fluid (CSF).

3. A process for producing the monoclonal antibody of claim 1 which involves:

culturing the hybridoma deposited at ECACC in Dec. 22, 1992 under No. 92122204 in an appropriate medium culture; and one of implanting the hybridomas into the peritoneum of a mouse, when ascites has been produced by the mouse, recovering the monoclonal antibodies then formed from said ascities; and recovering the monoclonal antibodies from the medium culture.

4. A kit comprising the monoclonal antibody of claim 1 and a buffer solution.

5. A monoclonal antibody AT270 secreted by the hybridoma deposited at ECACC on Jul. 7, 1993 under No. 93070774, which forms an immunological complex with a phosphorylated epitope of an antigen belonging to abnormally phosphorylated tau protein (PHF-tau) residing in the region spanning positions 143–254 with the following amino acid sequence:

```
                                        (SEQ ID NO 1)
          143                          150
NH₂- Lys Gly Ala Asp Gly Lys Thr Lys Ile Ala
                          160
Thr Pro Arg Gly Ala Ala Pro Pro Gly Gln Lys Gly
                  170
Gln Ala Asn Ala Thr Arg Ile Pro Ala Lys Thr Pro
          180
Pro Ala Pro Lys Thr Pro Pro Ser Ser Gly Glu Pro
      190                              200
Pro Lys Ser Gly Asp Arg Ser Gly Tyr Ser Ser Pro
                                  210
Gly Ser Pro Gly Thr Pro Gly Ser Arg Ser Arg Thr
                          220
Pro Ser Leu Pro Thr Pro Pro Thr Arg Glu Pro Lys
              230
Lys Val Ala Val Val Arg Thr Pro Pro Lys Ser Pro
          240
Ser Ser Ala Lys Ser Arg Leu Gln Thr Ala Pro Val
     250
Pro Met Pro Asp Leu Lys COOH
``` with said monoclonal antibody specifically detecting abnormally phosphorylated tau protein (PHF-tau) in cerebrospinal fluid (CSF).

6. A hybridoma deposited at ECACC on Jul. 7, 1993 under No. 93070774 which secretes a monoclonal antibody AT270 which forms an immunological complex with a phosphorylated epitope of an antigen belonging to abnormally phosphorylated tau protein (PHF-tau) residing in the region spanning positions 143–254 with the following amino acid sequence:

```
                                        (SEQ ID No 1)
          143                          150
NH₂- Lys Gly Ala Asp Gly Lys Thr Lys Ile Ala
                          160
Thr Pro Arg Gly Ala Ala Pro Pro Gly Gln Lys Gly
                  170
Gln Ala Asn Ala Thr Arg Ile Pro Ala Lys Thr Pro
          180
Pro Ala Pro Lys Thr Pro Pro Ser Ser Gly Glu Pro
```

-continued

```
        190                                         200
Pro Lys Ser Gly Asp Arg Ser Gly Tyr Ser Ser Pro

210
Gly Ser Pro Gly Thr Pro Gly Ser Arg Ser Arg Thr

220
Pro Ser Leu Pro Thr Pro Pro Thr Arg Glu Pro Lys

230
Lys Val Ala Val Val Arg Thr Pro Pro Lys Ser Pro

240
Ser Ser Ala Lys Ser Arg Leu Gln Thr Ala Pro Val

250
Pro Met Pro Asp Leu Lys COOH
``` with said monoclonal antibody specifically detecting abnormally phosphorylated tau protein (PHF-tau) in cerebrospinal fluid (CSF).

7. A process for producing the monoclonal antibody of claim 5 which involves:

culturing the hybridoma deposited at ECACC in Jul. 7, 1993 under No. 93070774 in an appropriate medium culture; and one of implanting the hybridomas into the peritoneum of a mouse, when ascites has been produced by the mouse, recovering the monoclonal antibodies then formed from said ascites; and recovering the monoclonal antibodies from the medium culture.

8. A kit comprising the monoclonal antibody of claim 5 and a buffer solution.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 112 amino acids
      (B) TYPE: amino acid
      (D) TOPOLOGY: linear    (ii) MOLECULE TYPE: peptide    (xi) SEQUENCE DESCRIPTION: SEQ ID NO: 1:

```
Lys Gly Ala Asp Gly Lys Thr Lys Ile Ala Thr Pro Arg Gly Ala Ala
1               5                   10                  15

Pro Pro Gly Gln Lys Gly Gln Ala Asn Ala Thr Arg Ile Pro Ala Lys
            20                  25                  30

Thr Pro Pro Ala Pro Lys Thr Pro Pro Ser Ser Gly Glu Pro Pro Lys
            35                  40                  45

Ser Gly Asp Arg Ser Gly Tyr Ser Ser Pro Gly Ser Pro Gly Thr Pro
            50                  55                  60

Gly Ser Arg Ser Arg Thr Pro Ser Leu Pro Thr Pro Pro Thr Arg Glu
65                  70                  75                  80

Pro Lys Lys Val Ala Val Val Arg Thr Pro Pro Lys Ser Pro Ser Ser
                85                  90                  95

Ala Lys Ser Arg Leu Gln Thr Ala Pro Val Pro Met Pro Asp Leu Lys
            100                 105                 110
```

(2) INFORMATION FOR SEQ ID NO: 2:

(i) SEQUENCE CHARACTERISTICS:
      (A) LENGTH: 5 amino acids
      (B) TYPE: amino acid
      (D) TOPOLOGY: linear    (ii) MOLECULE TYPE: peptide    (xi) SEQUENCE DESCRIPTION: SEQ ID NO: 2:

```
Val Arg Thr Pro Pro
1               5
```

(2) INFORMATION FOR SEQ ID NO: 3:

(i) SEQUENCE CHARACTERISTICS:
      (A) LENGTH: 5 amino acids
      (B) TYPE: amino acid
      (D) TOPOLOGY: linear    (ii) MOLECULE TYPE: peptide    (xi) SEQUENCE DESCRIPTION: SEQ ID NO: 3:

```
Pro Lys Thr Pro Pro
1               5
```